United States Patent [19]
Bentele

[11] 4,161,175
[45] Jul. 17, 1979

[54] SURGICAL FINGER AND FENCE SPLINTS

[75] Inventor: Max Bentele, Fairfield, Conn.

[73] Assignee: Conco Medical Co., Inc., Bridgeport, Conn.

[21] Appl. No.: 792,311

[22] Filed: Apr. 29, 1977

[51] Int. Cl.² ............................................. A61F 5/04
[52] U.S. Cl. .................................. 128/87 A; 128/89 R
[58] Field of Search ............... 128/87 A, 87 R, 89 R, 128/90

[56] References Cited

U.S. PATENT DOCUMENTS

| 2,273,028 | 2/1942 | Eaton | 128/87 A |
| 2,528,456 | 10/1950 | Stevenson | 128/87 A |
| 3,794,019 | 2/1974 | Ritland et al. | 128/87 A |
| 3,943,923 | 3/1976 | Scheinberg | 128/89 R |

FOREIGN PATENT DOCUMENTS

| 1286288 | 12/1962 | France | 128/89 R |
| 861081 | 2/1961 | United Kingdom | 128/89 R |

Primary Examiner—John D. Yasko
Attorney, Agent, or Firm—Wooster, Davis & Cifelli

[57] ABSTRACT

Surgical splints, including finger splints and fence splints, have thin and lightweight bases incorporating stiffening ribs to provide the stiffness and strength of thicker, heavier splints. Splints have aluminum bases with corrugated stiffening ribs, and plastic bases with integral stiffening ribs, wherein the plastic is rigid at room temperature and moldable at slightly higher temperatures. Additional splints have hand moldable plastic bases with metal wire, braided metal wire or wire mesh encapsulated therein to provide stiffness. The splints have more stiffness along their length than across their width. Splint pads are attached to splint bases by double-stick tape or removably attached by statistical loop fasteners.

14 Claims, 26 Drawing Figures

U.S. Patent  Jul. 17, 1979  Sheet 1 of 4  4,161,175
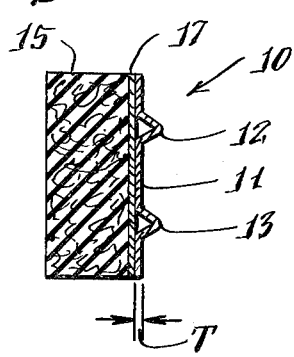
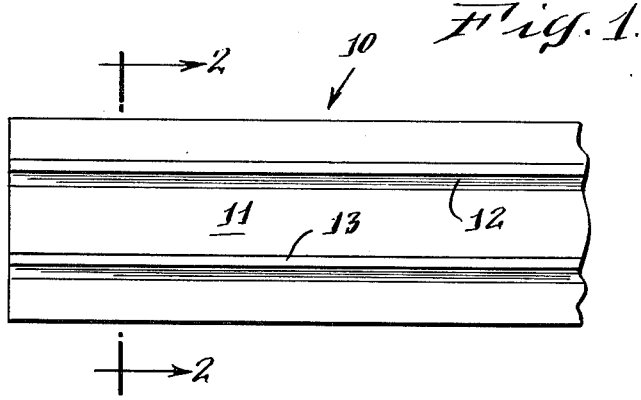
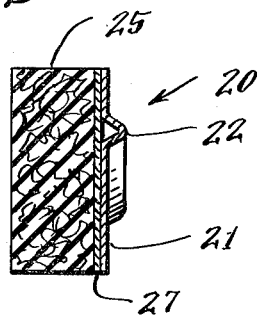
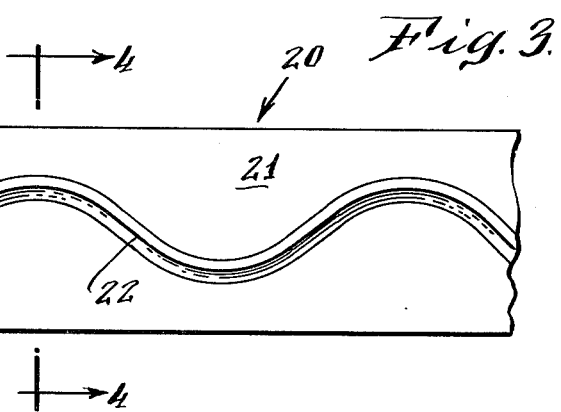
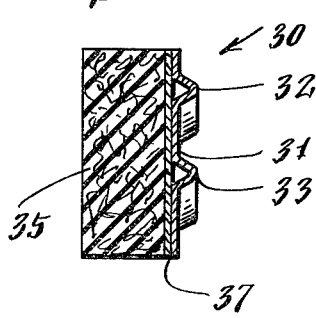
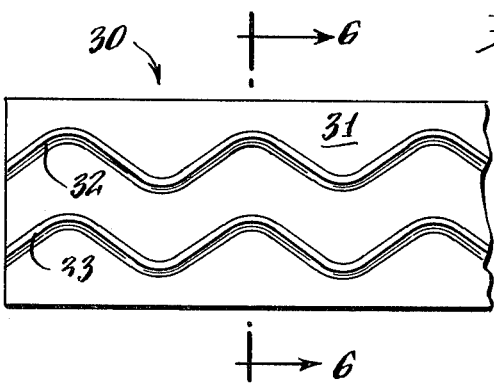
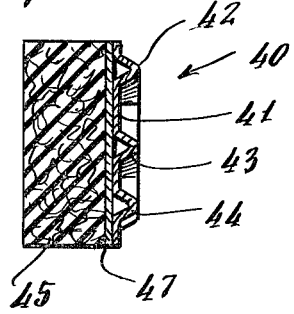
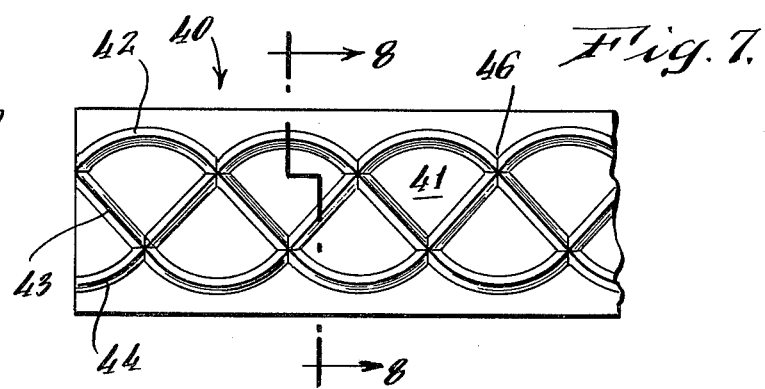

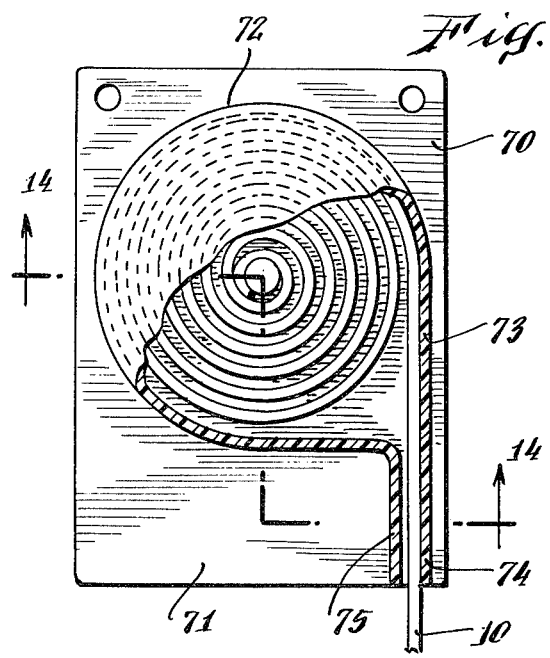
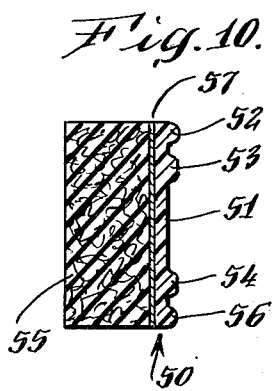
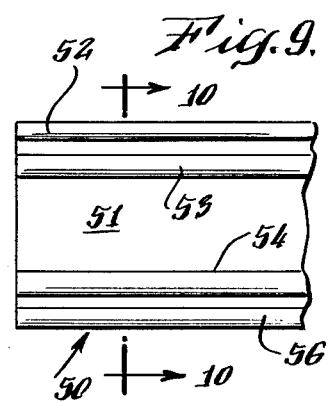
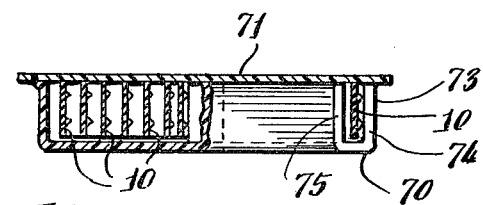
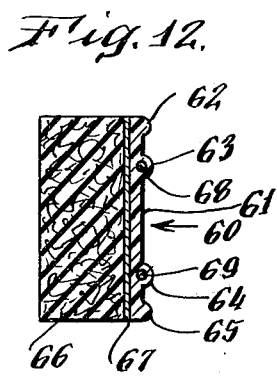
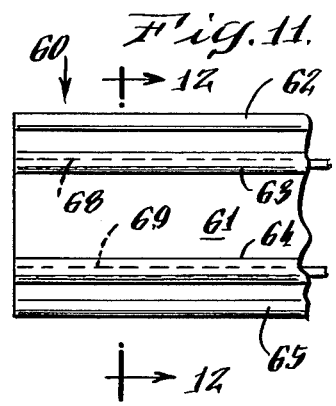
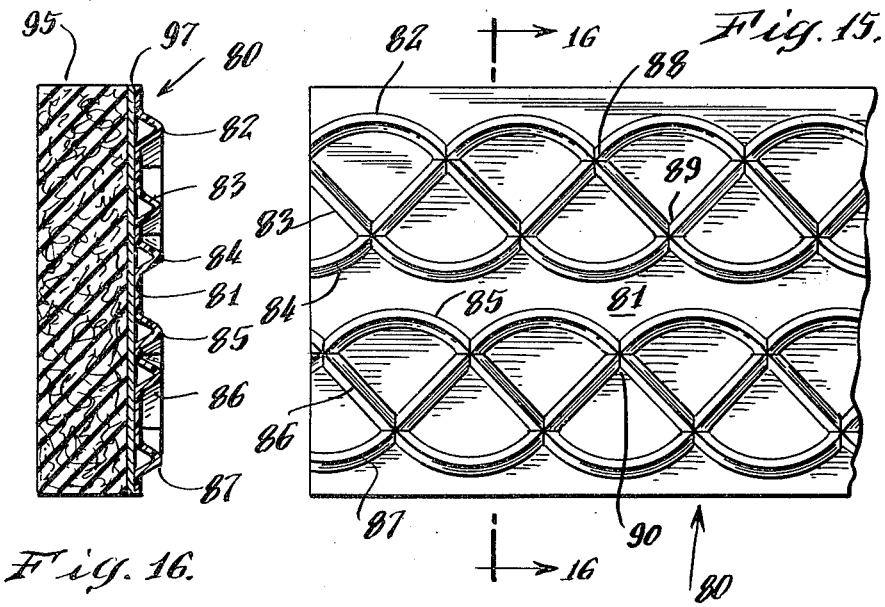
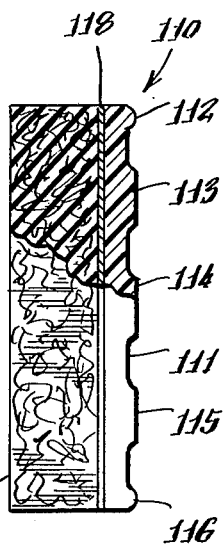

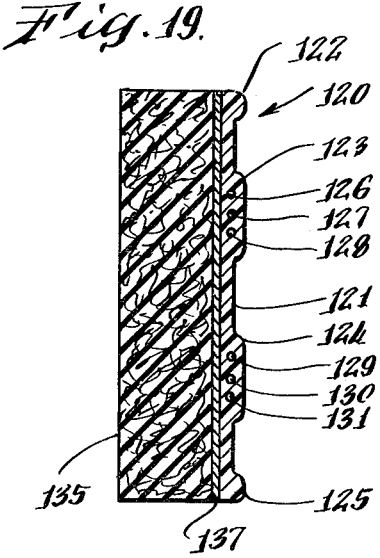
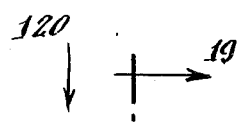
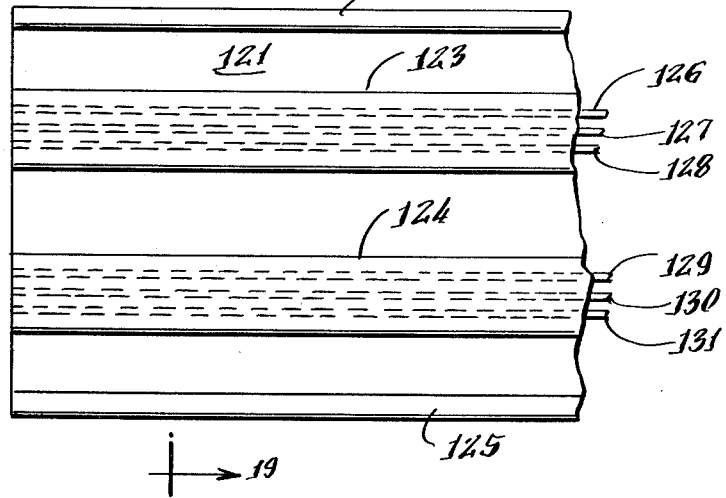
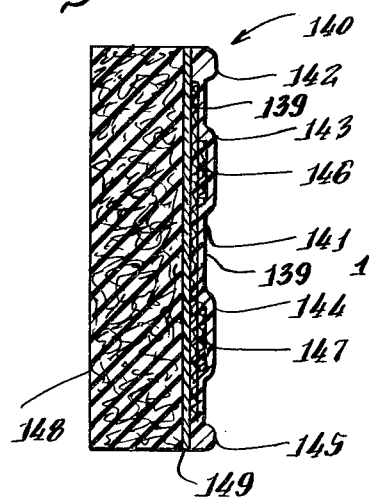
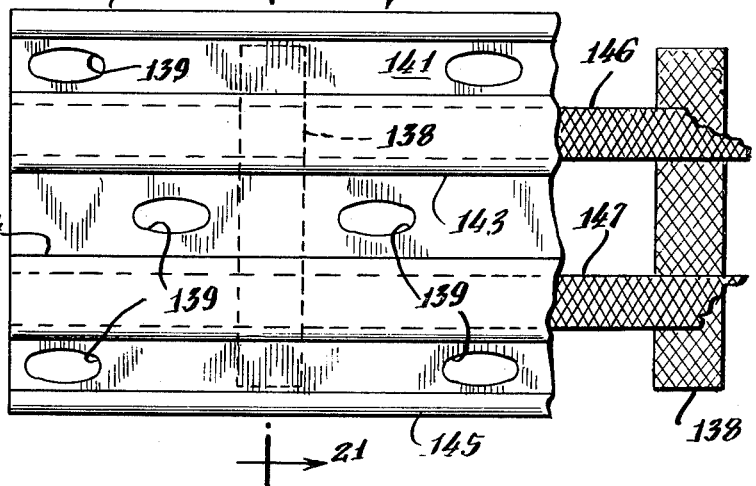
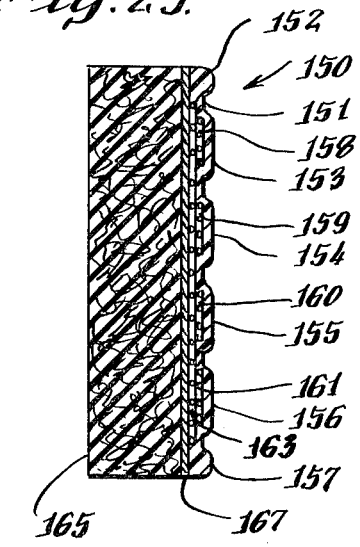
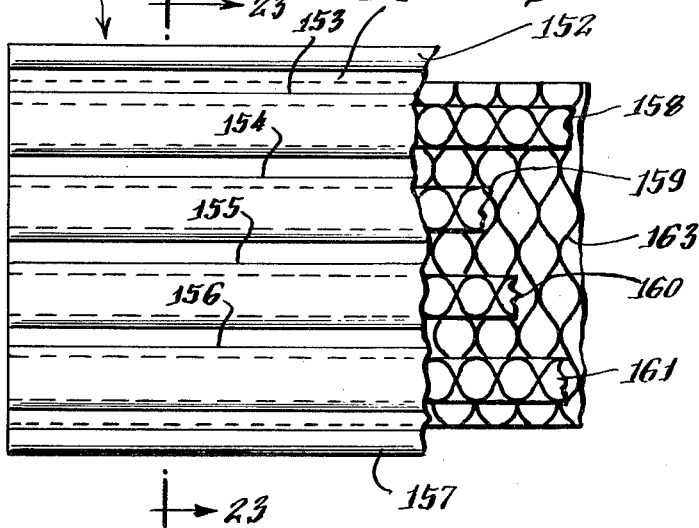

SURGICAL FINGER AND FENCE SPLINTS

BACKGROUND OF THE INVENTION

This invention relates to surgical finger and fence splints for use in immobilizing various parts of the body, such as fingers and arms.

Finger splints are presently comprised of aluminum sheet strip approximately one-half to one inch wide and 0.030 inch thick. A foam rubber pad is glued to the aluminum sheet strip by hand. The strip, with the foam attached, is cut to lengths of approximately nine to twelve inches and packaged for shipment.

Fence splints are manufactured in a similar manner. The aluminum sheet strip used in fence splints is generally 0.050 inch thick, and is cut to sizes approximately two to four inches in width and sixteen inches in length. A special splint design is disclosed in U.S. Pat. No. 2,958,325, wherein the aluminum sheet strip is provided with straight scores which reduce the stiffness and increase the formability perpendicular to the direction of the straight scores.

There are several inherent limitations and disadvantages associated with such prior art splints. First, because they are fabricated of relatively thick aluminum sheet material, they ae difficult to cut to size for final fitting to the patient. It is also difficult to obtain good x-rays without removing the splints, again because of the thickness of the aluminum sheet material. The weight of such splints is often uncomfortable to the patient, bearing in mind that the splints are being applied to an injured area. The thickness of the aluminum sheet material also increases the material costs of manufacturing such splints.

Additional disadvantages are caused by the hand-glued foam padding. Because the padding is permanently attached to the splint, when the foam padding becomes soiled and unsanitary the entire splint must be discarded. Then a new splint must be formed to immobilize the injured area; however, it is difficult to duplicate the precise shape of the original splint, with the result that the injured member is not held in the same position at it was with the original splint. It is desirable to immobilize the injured member in one position throughout the time necessary for healing. Hand gluing the foam pads to the splints is also an inefficient metod of manufacture.

SUMMARY OF THE INVENTION

Fence and finger splints according to the invention herein overcome many of the objections to the prior art splints. In particular, the invention provides an improved base for the splints. In one instance, the base is an aluminum sheet strip which is substantially thinner than prior art splints and is provided with corrugated ridges to attain approximately the same stiffness as the prior art splints. The corrugated ridges can be straight or curved, and may be crossed or may intersect to provide lengthwise and crosswise stiffness. Alternatively, the bases for the splints can be made from a plastic material which is moldable at temperatures only slightly above room temperature and at which the material can be comfortably and easily handled. These plastic splint bases can be provided with integral stiffening ribs, and in addition can include metal wire or mesh to increase the rigidity thereof without adding substantially to the weight. Additionally, splint bases of plastic which are not rigid at room temperature, but are instead somewhat pliable or moldable, are provided with metal wire or mesh reinforcement so that th splint bases can be formed to and hold a desired shape. The metal wire or mesh is preferably deployed so that the splint bases are more rigid along their longitudinal axes than they are across their widths, and the other embodiments described above also preferably incorporate this feature.

It will be appreciated that, in general, fence splints are thicker than finger splints as they must provide greater support over a larger area, but reductions in thicknesses of both over their respective prior art counterparts are achieved by the splint bases of this invention.

Both the aluminum and plastic splint bases are easily formable to the desired supportive shape, are lightweight and achieve reductions in material costs, yet result in a rigid splint. Each can also be provided with openings to make splints even lighter, and also make the splints air permeable. Splints with the foregoing base materials are easily trimmed to desired shapes, and narrow splints can be cut from wide splints, as desired.

Splints according to the invention also incorporate improvements in attaching foam padding to the base of the splint. In some splints, and particularly fence splints, a two-piece statistical loop fastener is used to attach the foam padding to the base of the splint. If it is necessary to change the foam padding, a new pad having attached thereto the appropriate portion of a statistical loop fastener can be substituted for the original pad. The original splint base, already formed to the desired shape, is retained. In instances where removal and/or replacement of the foam pad is not desired, the foam pad can be attached to the splint base by means of a double-sided tape with great savings in efficiency of manufacture.

OBJECTS

It is a principal object of the invention to provide improved surgical splints.

It is an additional object of the invention to provide improved surgical finger and fence splints which can be shaped and applied quickly and easily.

It is a further object of the invention to provide improved surgical finger and fence splints which are lightweight and more comfortable to the patient, and are nevertheless strong.

It is yet another object of the invention to provide improved surgical splints which can be produced at reduced material and manufacturing costs.

Other and more specific objects of the invention will in part be obvious to those skilled in the art and will in part appear from the following description of the preferred embodiments and the claims, taken together with the drawings.

DRAWINGS

FIG. 1 is a plan view, partially cut away, of a finger splint according to the invention herein;

FIG. 2 is a sectional view of the finger splint of FIG. 1 taken along the lines 2—2 of FIG. 1;

FIG. 3 is a plan view, partially cut away, of another finger splint according to the invention herein;

FIG. 4 is a sectional view of a finger splint of FIG. 3 taken along the lines 4—4 of FIG. 3;

FIG. 5 is a plan view, partially cut away, of another finger splint according to the invention herein;

FIG. 6 is a sectional view of the finger splint of FIG. 5 taken along the lines 6—6 of FIG. 5;

FIG. 7 is a plan view, partially cut away, of another finger splint according to the invention herein;

FIG. 8 is a sectional view of a finger splint of FIG. 7 taken along the lines 8—8 of FIG. 7;

FIG. 9 is a plan view, partially cut away, of another finger splint according to the invention herein;

FIG. 10 is a sectional view of the finger splint of FIG. 9 taken along lines 10—10 of FIG. 9;

FIG. 11 is a plan view, partially cut away, of another finger splint according to the invention herein;

FIG. 12 is a sectional view of the finger splint of FIG. 11 taken along the lines 12—12 of FIG. 11;

FIG. 13 is a top view of a finger splint according to the invention herein in a dispenser package;

FIG. 14 is a sectional view of the finger splint and dispenser package of FIG. 13 taken along the lines 14—14 of FIG. 13;

FIG. 15 is a plan view, partially cut away, of a fence splint according to the invention herein;

FIG. 16 is a sectional view of the fence splint of FIG. 15 taken along the lines 16—16 of FIG. 15;

FIG. 17 is an end view, partially in section, of another fence splint according to the invention herein;

FIG. 18 is a plan view, partially cut away, of another fence splint according to the invention herein;

FIG. 19 is a sectional view of the fence splint of FIG. 18 taken along the lines 19—19 of FIG. 18;

FIG. 20 is a plan view, partially cut away, of another fence splint according to the invention herein;

FIG. 21 is a sectional view of the fence splint of FIG. 20 taken along the lines 21—21 of FIG. 20;

FIG. 22 is a plan view, partially cut away, of another fence splint according to the invention herein;

FIG. 23 is a sectional view of the fence splint of FIG. 22 taken along the lines 23—23 of FIG. 22;

The same reference numerals refer to the same elements throughout the various Figures.

DESCRIPTION OF THE PREFERRED EMBODIMENTS

Figure 24:
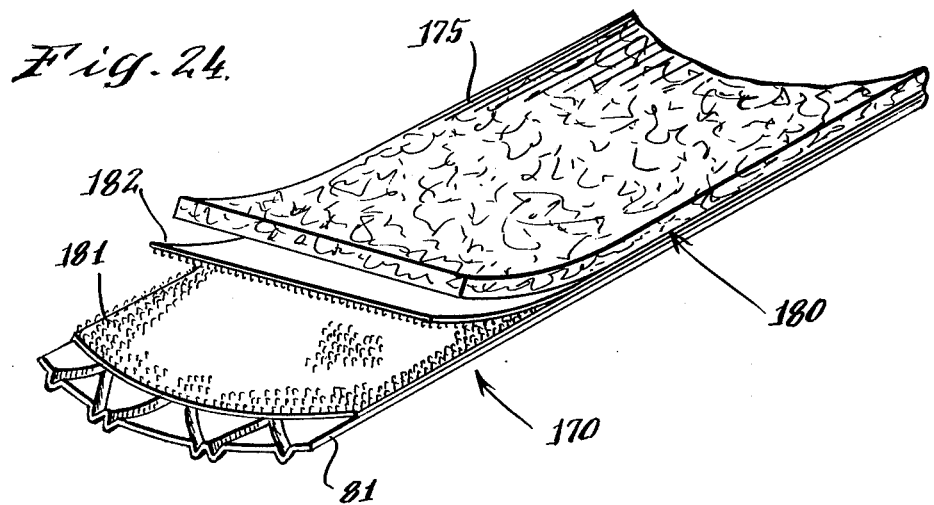
FIG. 24 is a perspective view of another fence splint according to the invention herein.

Finger splints according to the invention herein are shown in FIGS. 1-12, and one of the finger splints is shown in a dispenser package in FIGS. 13 and 14. Fence splints according to the invention herein are shown in FIGS. 15-26.

All of the splints according to the invention herein comprise a base with foam padding attached to one side thereof, wherein the base is thinner and/or lighter than in prior art splints. Sufficient stiffness of the splints is achieved through providing stiffening ribs in the base portions more fully described below with respect to specific embodiments. Some of the splints incorporate means for removably attaching foam padding to the bases, and some have foam padding attached by double-stick tape, thereby providing advantages over the prior art.

A first finger splint 10 according to the invention herein is illustrated in FIGS. 1 and 2. It comprises a base 11, a layer of foam padding 15 and a layer of double-stick tape 17 which attaches the foam padding 15 to the base 11. The base 11 is fabricated of aluminum sheet material which is preferably approximately 0.020 inch thick and may be in the range of about 0.010 to 0.025 inch thick. Two corrugated stiffening ribs 12 and 13 are formed lengthwise in the aluminum base 11, and the stiffening ribs 12 and 13 strengthen the finger splint 10 along its length such that it is lengthwise approximately of the same stiffness as if fabricated from aluminum sheet material approximately 0.030 inch thick. The splint is less stiff across its width and thus can be adapted more readily to an injured finger, an advantage not possible with a prior art splint having a base of uniform thickness. The corrugations in the aluminum sheet can be formed by passing the aluminum sheet through a forming station comprising a rotating cylindrical press having corrugation-forming protrusions and a base die positioned therebelow. This type of operation is well-known and is also applicable to manufacturing other splints described below. The finger splint 10 is shown partially cut away in FIG. 1, and it may be manufactured in long lengths, e.g. on the order of ten feet or more. Its width may be approximately one-half inch. It may be cut to lengths of approximately nine to twelve inches and packaged for shipment, or it may be packaged in longer lengths, and in either event it is easily cutable, because of its thinness, to a desired length for application to an injured finger.

Referring now to FIGS. 3 and 4, another finger splint 20 according to the invention herein is shown. It is comprised of a base 21 having a foam pad 25 attached thereto by a double-stick tape 27. The base 21 is provided with a corrugated stiffening rib 22 having a generally sinusoidal configuration, whereby the corrugated stiffening rib 22 contributes to both lengthwise and widthwise stiffness of the finger splint 20, although it still has more stiffness lengthwise than widthwise. The base 21 may, therefore, be fabricated of relatively thin aluminum stock, in the range of 0.010 to 0.025 inch thick, and yet exhibit sufficient stiffness to function well as a finger splint. It may be manufactured and packaged in any desired lengths, and is easily cut to useful sizes.

FIGS. 5 and 6 illustrate another finger splint 30 according to the invention herein and generally comprising a base 31, a foam pad 35 and a layer of double-stick tape 37 attaching the foam pad 35 to the base 31. Two spaced apart and generally parallel sinusoidal corrugated stiffening ribs 32 and 33 extend lengthwise along the base of finger splint 30 to increase its longitudinal stiffness. Again, the base is fabricated of relatively thin aluminum sheet material, its thickness being in the range of approximately 0.010 to 0.025 inch and preferably approximately 0.020 inch, wherein the finger splint 30 is easily cutable, has sufficient strength to support an injured finger, and is easily bendable to the desired configuration.

Referring now to FIGS. 7 and 8, a finger splint 40 also according to the invention herein generally comprises a base 41 and a foam pad 45 held to the base 41 by double-stick tape 47. The base 41 has formed therein three corrugated sinusoidal ribs 42-44, each of which extends substantially the entire width and length of the finger splint 40. The sinusoidal ribs 42-44 intersect at various points along the finger splint 40, such as at point 46. This configuration of sinusoidal ribs provides a relatively strong and uniformly stiff finger splint although its base 41 is fabricated of relatively thin aluminum sheet material having a thickness in the range of approximately 0.010 to 0.025 inch. As with the previously described finger splints, finger splint 40 is readily cutable to a desired length and bendable to a desired shape for supporting an injured finger.

FIGS. 9 and 10 illustrate yet another finger splint 50 according to the invention herein. It comprises a base 51 having a foam pad 55 attached thereto by a double-stick tape 57. The base 51 is fabricated of a plastic material, and is provided with integral longitudinal stiffening ribs 52, 53, 54 and 56. Although the stiffening ribs 52, 53 and 54, 56 are shown disposed adjacent to the side edges of the finger splint 50, it will be appreciated that they could be deployed evenly across the width thereof, or in other desired configurations. The plastic from which base 51 is fabricated is preferably of a type which is substantially rigid at environmental temperatures in the range of approximately 90° F. and lower, but which softens at temperatures slightly above environmental temperatures, for instance at temperatures in the range of approximately 110° to 125° F. or slightly higher. Thus, the finger splint can be heated slightly and formed to the desired shape, and even at forming temperatures the splint is not uncomfortable to handle or to place against the patient for fittting.

The plastic material from which the base 51 is fabricated may be ethylene-vinyl acetate copolymers, and other plastics having utility for this purpose are polycaprolactones, polyterpenes, styrene copolymers and blends thereof, as well as others. The particular plastic is not critical, as many are advantageously applicable and readily formulated for the specific purposes of the finger splints described herein.

Referring now to FIGS. 11 and 12, a finger splint 60 according to the invention herein is shown. The finger splint 60 generally comprises a base 61 and a foam pad 66 which is held to the base 61 by means of a layer of double-stick tape 67. The base 61 is preferably fabricated of plastic which is moldable or formable at room temperature, such as some polyethylenes, urethane elastomers, and a wide selection of others. The base 61 is provided with four stiffening ribs 62–65 which extend longitudinally along the finger splint 60. The stiffening ribs 63 and 64 are provided with stiffening wires 68 and 69, respectively, and the stiffening wires 68 and 69 are molded in and encased by the stiffening ribs 63 and 64 of base 61. The wires 68 and 69 provide rigidity or stiffness for the finger splint 60 when it is molded to the desired shape, and are bendable so that the finger splint can be molded to the desired shape by hand manipulation. This finger splint is advantageous over finger splint 50 as it does not require heating to shape it.

In the foregoing finger splints, the foam pads thereof were described as being attached to the bases with double-stick tape. This is preferable over the prior art method of hand gluing a foam pad to the base of a splint because of the greater convenience in assembly and the uniformity of adherence between the foam pad and the splint base. However, it will be understood that the advantages of the novel configurations of splint bases and particularly the stiffening structures thereof can be attained even if the foam padding were attached by the traditional hand gluing method, or by a mechanized gluing method.

Referring now to FIGS. 13 and 14, there is illustrated a package 70 for a finger splint 10 described above. The package 70 generally comprises a bottom plate 71, a top plate 72 and a connecting wall 73. The end portions 74 and 75 of the connecting wall 73 are juxtaposed to provide an exit slot for the finger splint 10, and the remaining portion of connecting wall 73 is generally circular wherein a coil of the finger splint 10 is accommodated. Thus, a desired length of the finger splint 10 can be pulled out of the package and cut off for application to the patient. A supply of the finger splint is maintained in a coil in the package 70, where it is kept clean, dry and available for use. The top 72 of the package 70 is preferably transparent so that the supply of finger splints is visually ascertainable. The package 70 is also useful in conjunction with finger splints 20, 30 and 40 described above, and can also be used with finger splints 50 and 60 by heating the entire package and coil of finger splints prior to unrolling a section thereof.

Fence splints according to the invention herein are illustrated in FIGS. 15–26. Fence splints are primarily for application to injured arms, and are similar to but larger than the finger splints described above. Typically, fence splints are provided in widths of approximately two to four inches and lengths of approximately sixteen inches. As an example of the similarity between finger splints and fence splints according to the invention herein, a fence splint could comprise a base having a foam pad attached thereto wherein the base has a plurality of longitudinally extending corrugated straight stiffening ribs, similar to finger splint 10 described above, except larger. It will also be appreciated that fence splints have generally been made of slightly thicker base material, such as aluminum sheet approximately 0.050 inch thick. Substantial reductions in the thickness of the base material can be achieved with the stiffening structures of the invention herein, and aluminum sheet base material of at least 0.020 inch and preferably in the range of 0.020 to 0.035 inch is desirable in fabricating fence splints according to the invention herein, as well as other base materials described below.

Referring now to FIGS. 15 and 16, a fence splint 80 according to the invention herein is shown. It generally comprises a base 81 having a foam pad 95 attached thereto by means of double-stick tape 97. The base 81 is provided with six corrugated stiffening ribs 82–87 which are deployed in two sets, the first set comprising stiffening ribs 82–84 and the second set comprising stiffening ribs 85–87. Each of the stiffening ribs is generally sinusoidal when viewed in plan, and extends along the length and width of the fence splint, with the "peaks" of the sinusoidal curve falling near the edges and the center of the fence splint. The stiffening ribs intersect at various points on the fence splint 80, such as the intersection of corrugated ribs 83 and 84 at point 88, the intersection of corrugated ribs 82 and 84 at 89, and the intersection of corrugated ribs 86 and 87 at 90. It will be noted that the "peaks" of the corrugated stiffening ribs are staggered such that the intersection points between the corrugated ribs are also staggered along the length of the fence splint 80, e.g. the intersection points 88, 89 and 90 are staggered along the length of fence splint 80, which promotes uniform rigidity. The configuration of the stiffening ribs, however, provides a splint which has greater stiffness along its length where greater stiffness is desired, and has somewhat less stiffness across its width where less stiffness is required, and this facilitates forming the splint to the patient's injured arm. The base 81 of fence splint 80 is preferably fabricated of aluminum sheet approximately 0.025 inch thick, wherein it is easily cutable and yet rigid by virtue of the corrugated stiffening ribs 82–87.

A fence splint 110 according to the invention herein is shown in section in FIG. 17. It generally comprises a base 111 having a foam pad 117 attached thereto by means of double-stick tape 118. The base 111 is preferably fabricated of a plastic material which is rigid at room temperature and moldable at slightly above room temperature, such as described above, and is provided with a series of longitudinally extending integral stiffening ribs 112-116. The thinner portions of the base 111 between the stiffening ribs 112-116 soften first and facilitate bending the fence splint 110 across its width, while the stiffening ribs 112-116 provide longitudinal strength.

FIGS. 18 and 19 illustrate a fence splint 120, also according to the invention herein. It generally comprises a base 121 having a foam pad 135 attached thereto by means of double-stick tape 137. Base 121 is fabricated of a plastic material which is moldable at room temperature, and it is provided with integral longitudinal stiffening ribs 122 and 125 along the outside edge of the fence splint 120 and additional integral longitudinal stiffening ribs 123 and 124 intermediate the fence splint 120. The intermediate stiffening ribs 123 and 124 are molded about and encapsulate metal wires 126-128 and 129-131, respectively, and the metal wires provide rigidity to the splint and maintain it in the desired configuration for application to an injured arm. The fence splint 120 has greater rigidity along its length, as desired, than across its width.

The fence splint 140 illustrated in FIGS. 20 and 21, also according to the invention herein, is similar and comprises a plastic base 141 having integral longitudinal stiffening ribs 142-145, the central ribs 143, 144 encapsulating wire mesh strips 146, 147, respectively. Additional wire mesh strips 138 are deployed crosswise at intervals along the base 141, and wire mesh strips 138 are also encapsulated in the base plastic. A foam pad 148 is attached by double-stick tape 149. Openings 139 formed in the base 141 reduce its weight, and the stiffening ribs 142-145 and mesh strips 146, 147 maintain the rigidity of the splint, which is greater longitudinally than widthwise.

A fence splint 150 according to the invention herein is illustrated in FIGS. 22 and 23, and it is also similar to fence splints 120 and 140. Fence splint 150 generally comprises a base 151 having spaced-apart integral longitudinal stiffening ribs 152-157. The base 151 is preferably fabricated of plastic of the type which is moldable at room temperature, and the plastic is molded about and surrounds strips of braided wire 158-161. In particular, the stiffening rib 153 is molded about braided wire 158, the stiffening rib 154 is molded about braided wire 159, the stiffening rib 155 is molded about braided wire 160, and the stiffening rib 156 is molded about braided wire 161. A wide strip of braided wire 163 underlies the strips 158-161 to contribute to both the lengthwise and widthwise stiffness of splint 150, the lengthwise stiffness being greater. A foam pad 165 is attached to the base 151 by double-stick tape 167 to complete fence splint 150.

Figure 25:
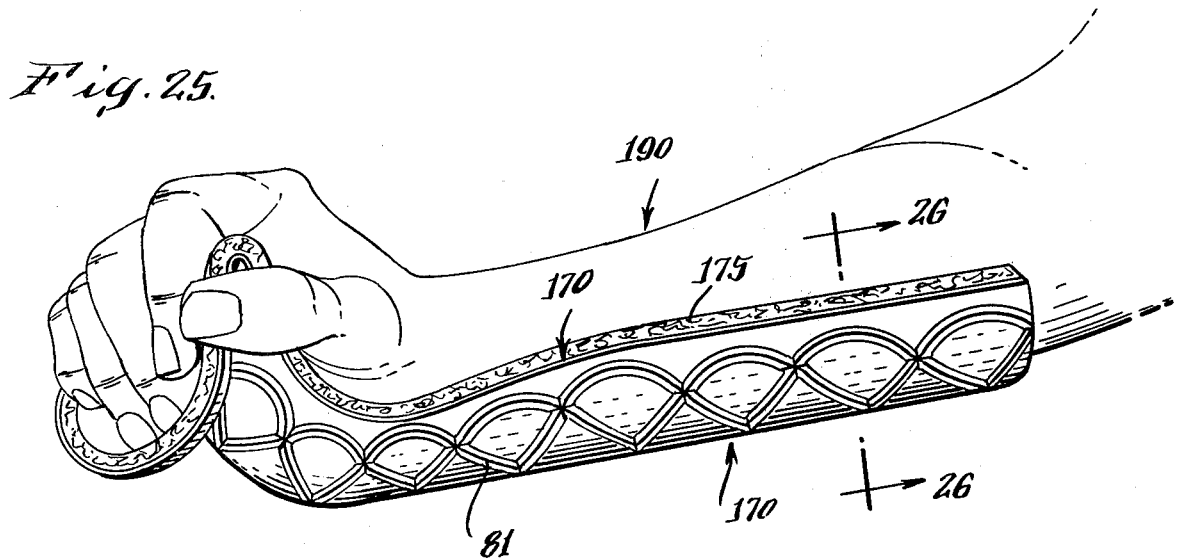
FIG. 25 is a perspective view of the fence splint of FIG. 24 applied to the arm of a patient.
Figure 26:
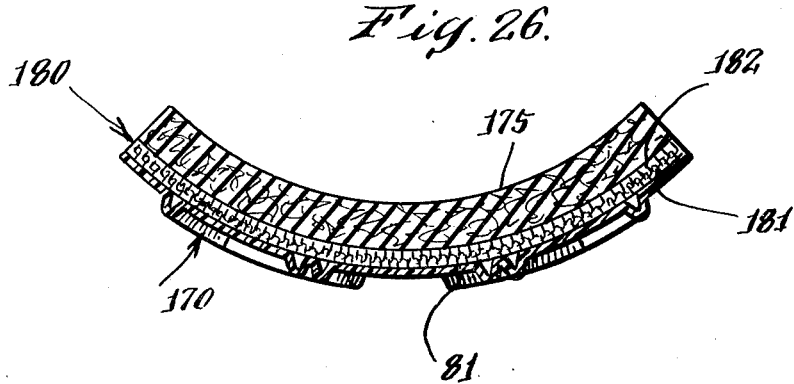
FIG. 26 is a sectional view of the fence splint of FIG. 25 taken along the lines 26—26 of FIG. 25.

Another fence splint 170 is illustrated in FIGS. 24-26. The fence splint 170 comprises a base 81 (which is the same as the base 81 of fence splint 80). The bases 111, 121, 141 and 151 of fence splints 110, 120, 140 and 150 described above would also be suitable for use in fabricating fence splint 170. Fence splint 170 is provided with a foam pad 175 which is removably attached to the base 81 by means of a statistical loop fastener 180, which may be of the type sold under the trademark Velcro. In particular, one portion 181 of the statistical loop fastener 180 is secured to the base 81 by means of glue, double-stick tape, or other suitable means. The other portion 182 of the statistical loop fastener 180 is applied to one side of the foam pad 175 with attachment also being carried out by means of glue, double-stick tape or the like. The foam pad 175 is then attached to the base 81 by pressing the two portions 181 and 182 of the statistical loop fastener together.

Referring particularly to FIG. 25, the fence splint 170 is shown formed to shape and applied to the arm 190 and hand of a patient. It will be noted that the fence splint 170 is bent across its width to partially surround the arm, as also seen in the FIG. 26 sectional view of the fence splint 170 above. In addition, the fence splint 170 is bent along its length to accept and support the hand and fingers of the patient.

It is desirable that the injured member be maintained in substantially the same position throughout the time necessary for it to heal. It will be appreciated that it is difficult to bend a fence splint to an identical form of a previous fence splint. However, it has been necessary to attempt to do so with prior art splints when the foam pad became sufficiently soiled and unsanitary that it had to be discarded. The fence splint 170 incorporating a statistical loop fastener 180 overcomes this problem. The foam pad 175 and the attached second portion 182 of the statistical loop fastener is merely removed from the base 81 and first portion 181 of the statistical loop fastener 180, and is replaced by a new foam pad. The new foam pad, of course, is provided with the appropriate portion of a statistical loop fastener for ready application to the base.

It will be appreciated that the other fence splints described herein are applied in a manner similar to that illustrated in FIG. 25, and that the feature of a removable foam pad attached to the splint base by a statistical loop fastener can also be utilized with the bases of the other fence splints described herein. It will also be appreciated that finger splints can be constructed in a manner similar to fence splints 120, 140 and 150, i.e., having bases made of a plastic which is hand moldable at room temperature, with stiffness supplied by wire, which may be wire mesh or braided wire, encapsulated in the plastic bases. Such finger splints can also be placed in a dispenser package such as shown in FIGS. 13 and 14.

All of the surgical splints according to the invention herein and described above, including both finger splints and fence splints, are light in weight, yet strong, and are easily cut to desired size and are also easily fitted to a patient. They are also relatively simple to manufacture, and achieve savings in materials. Accordingly, they efficiently accomplish the objects of the invention herein. It will be appreciated that modifications to the preferred embodiments described above can be made without departing from the spirit and scope of the invention, which is limited only by the following claims.

I claim:

1. A surgical splint comprising a supportive base fabricated of bendable aluminum sheet material, the base having at least one integral stiffening rib comprising a corrugated portion of the bendable aluminum sheet material, the integral stiffening rib disposed in a preselected pattern extending across both the width and length of the base thereby increasing both the widthwise and longitudinal rigidity of the bendable aluminum sheet material, and a foam pad attached to the base on the side opposite the at least one corrugated stiffening rib.

2. A surgical splint as defined in claim 1 wherein the foam pad is removably attached to the base.

3. A surgical splint as defined in claim 2 wherein the foam pad is removably attached to the base by means of a two-piece statistical loop fastener, one piece of the statistical loop fastener attached to the base and the other piece of the statistical loop fastener attached to the foam pad.

4. A surgical splint as defined in claim 1 wherein the integral stiffening rib is curved.

5. A surgical splint as defined in claim 4 wherein the curved integral stiffening rib defines a generally sinusoidal curve.

6. A surgical splint as defined in claim 4 wherein said at least one curved stiffening rib comprises a plurality of curved integral stiffening ribs.

7. A surgical splint as defined in claim 6 wherein each of the plurality of curved integral stiffening ribs defines a generally sinusoidal curve, and the plurality of integral stiffening ribs are evenly spaced apart.

8. A surgical splint as defined in claim 6 wherein the curved integral stiffening ribs intersect at a plurality of points.

9. A surgical splint as defined in claim 8 wherein the points at which the curved integral stiffening ribs intersect are staggered along the length of the surgical splint.

10. A surgical splint as defined in claim 9 wherein each of the plurality of integral stiffening ribs defines a generally sinusoidal curve.

11. A surgical splint as defined in claim 1 wherein said at least one integral stiffening rib comprises a plurality of integral stiffening ribs which intersect at a plurality of points.

12. A surgical splint as defined in claim 1 wherein the splint is dimensioned for use as a finger splint and the aluminum sheet material has a thickness in the range of 0.010 to 0.025 inch.

13. A surgical splint as defined in claim 1 wherein the splint is dimensioned for use as a fence splint and the aluminum sheet material has a thickness in the range of 0.020 to 0.035 inch.

14. A surgical splint as defined in claim 1 wherein the foam pad is attached to the base by means of tape having adhesive on both sides thereof.

* * * * *